United States Patent
Farmer et al.

(10) Patent No.: US 9,622,502 B2
(45) Date of Patent: Apr. 18, 2017

(54) PROBIOTIC BACILLUS PASTA COMPOSITIONS

(75) Inventors: Sean Farmer, Miami Beach, FL (US); Andrew R. Lefkowitz, University Heights, OH (US); Michael Bush, Brecksville, OH (US); David Maske, Chagrin Falls, OH (US)

(73) Assignee: GANEDEN BIOTECH, INC., Mayfield Heights, OH (US)

( * ) Notice: Subject to any disclaimer, the term of this patent is extended or adjusted under 35 U.S.C. 154(b) by 669 days.

(21) Appl. No.: 12/580,622

(22) Filed: Oct. 16, 2009

(65) Prior Publication Data

US 2010/0210000 A1     Aug. 19, 2010

Related U.S. Application Data

(60) Provisional application No. 61/106,116, filed on Oct. 16, 2008.

(51) Int. Cl.
| | |
|---|---|
| A61K 8/97 | (2006.01) |
| A23L 1/30 | (2006.01) |
| C12N 1/20 | (2006.01) |
| A23L 7/104 | (2016.01) |
| A23L 7/109 | (2016.01) |
| A23L 33/135 | (2016.01) |
| A23L 23/10 | (2016.01) |

(52) U.S. Cl.
CPC ............ *A23L 1/3014* (2013.01); *A23L 7/104* (2016.08); *A23L 7/109* (2016.08); *A23L 23/10* (2016.08); *A23L 33/135* (2016.08); *C12N 1/20* (2013.01); *A23V 2002/00* (2013.01)

(58) Field of Classification Search
CPC . A61K 8/97; A61K 35/74; A61K 8/99; A23V 2002/00; A23V 2200/3204; A23V 2200/324; A23V 2200/32; A23L 1/3014; A23L 2/39; A23L 3/3571; C12N 1/20
See application file for complete search history.

(56) References Cited

U.S. PATENT DOCUMENTS

| | | | |
|---|---|---|---|
| 3,091,572 A | 5/1963 | Luedemann et al. | |
| 3,840,684 A | 10/1974 | Fazzina et al. | |
| 4,110,477 A | 8/1978 | Naruse et al. | |
| 4,144,346 A | 3/1979 | Heeres et al. | |
| 4,278,690 A * | 7/1981 | Onodera ................. | A23G 9/42 426/18 |
| 4,321,258 A | 3/1982 | Dunlap | |
| 4,323,651 A | 4/1982 | Long et al. | |
| 4,695,546 A | 9/1987 | Aiba et al. | |
| 4,756,913 A | 7/1988 | Khorkova et al. | |
| 4,956,177 A | 9/1990 | King et al. | |
| 4,980,180 A | 12/1990 | Cully et al. | |
| 5,021,344 A | 6/1991 | Armau et al. | |
| 5,079,164 A | 1/1992 | Kirkovits et al. | |
| 5,102,800 A | 4/1992 | Hirikoshi | |
| 5,176,911 A | 1/1993 | Tosi et al. | |
| 5,200,336 A | 4/1993 | Kong et al. | |
| 5,266,315 A | 11/1993 | Taguchi et al. | |
| 5,413,960 A | 5/1995 | Dobrogosz et al. | |
| 5,439,678 A | 8/1995 | Dobrogosz et al. | |
| 5,439,995 A | 8/1995 | Bailly et al. | |
| 5,531,998 A | 7/1996 | Mares et al. | |
| 5,534,253 A | 7/1996 | Casas et al. | |
| 5,665,354 A | 9/1997 | Neyra et al. | |
| 5,785,990 A | 7/1998 | Langrehr | |
| 5,895,672 A | 4/1999 | Cooper | |
| 5,968,569 A | 10/1999 | Cavadini et al. | |
| 6,080,401 A | 6/2000 | Reddy et al. | |
| 6,132,710 A | 10/2000 | Panigrahi et al. | |
| 6,461,607 B1 | 10/2002 | Farmer | |
| 6,531,126 B2 | 3/2003 | Farmer | |
| 6,537,543 B1 | 3/2003 | Minakawa | |
| 6,706,290 B1 * | 3/2004 | Kajander ............... | A01N 35/02 422/1 |
| 6,723,326 B1 | 4/2004 | Farmer | |
| 6,835,397 B2 | 12/2004 | Lee et al. | |
| 6,849,256 B1 | 2/2005 | Farmer | |
| 7,024,497 B1 | 4/2006 | Maffezoni | |
| 7,374,753 B1 | 5/2008 | Farmer et al. | |
| 7,555,715 B2 | 6/2009 | Randall et al. | |
| 7,708,988 B2 | 5/2010 | Farmer | |
| 7,767,203 B2 | 8/2010 | Farmer et al. | |
| 7,807,151 B2 | 10/2010 | Farmer | |
| 8,097,247 B2 | 1/2012 | Farmer | |
| 8,187,590 B2 | 5/2012 | Farmer | |
| 8,821,854 B2 | 9/2014 | Farmer et al. | |
| 2003/0031659 A1 | 2/2003 | Farmer | |
| 2003/0138936 A1 | 7/2003 | Mizuguchi et al. | |

(Continued)

FOREIGN PATENT DOCUMENTS

| | | |
|---|---|---|
| CN | 1507812 A | 6/2004 |
| DE | 4132296 C1 | 12/1992 |
| EP | 1020123 A1 | 7/2000 |
| EP | 1344458 A1 | 9/2003 |
| EP | 1810579 A1 | 7/2007 |
| GB | 1040278 A | 8/1966 |
| JP | S45032905 | 10/1970 |
| JP | 64083025 | 3/1989 |
| JP | 4082827 A | 3/1992 |
| JP | 4158771 A | 6/1992 |
| JP | 6166626 A | 6/1994 |
| JP | 08175921 | 7/1996 |
| JP | H09107869 | 4/1997 |
| JP | H1084845 A | 4/1998 |
| JP | 11169145 A | 6/1999 |

(Continued)

OTHER PUBLICATIONS

ATCC Catalogue of Bacteria and Bacteriophages, Accession No. 31284.

(Continued)

*Primary Examiner* — Blaine Lankford
(74) *Attorney, Agent, or Firm* — Mintz Levin Cohn Ferris Glovsky and Popeo, P.C.

(57) ABSTRACT

The present application relates to probiotic grain-based compositions comprising lactic acid-producing bacteria.

15 Claims, 1 Drawing Sheet

(56) References Cited

U.S. PATENT DOCUMENTS

| | | |
|---|---|---|
| 2003/0185811 A1 | 10/2003 | Teasdale et al. |
| 2004/0010510 A1 | 1/2004 | Hotti |
| 2004/0071685 A1 | 4/2004 | Houston et al. |
| 2004/0161522 A1 | 8/2004 | Toves |
| 2004/0175459 A1 | 9/2004 | Ting |
| 2004/0197277 A1 | 10/2004 | Gonzales |
| 2005/0100535 A1 | 5/2005 | Farmer et al. |
| 2005/0153040 A1* | 7/2005 | Axelrod et al. .............. 426/516 |
| 2005/0154682 A1 | 7/2005 | Taylor |
| 2005/0202145 A1 | 9/2005 | Dorr et al. |
| 2005/0271643 A1 | 12/2005 | Sorokulova et al. |
| 2006/0099197 A1 | 5/2006 | Farmer |
| 2006/0112584 A1 | 6/2006 | Jones |
| 2006/0154350 A1* | 7/2006 | Kolbakov et al. ............ 435/139 |
| 2006/0177429 A1 | 8/2006 | Farmer et al. |
| 2006/0184538 A1 | 8/2006 | Randall et al. |
| 2006/0204633 A1 | 9/2006 | Moore |
| 2007/0059400 A1 | 3/2007 | Goto et al. |
| 2008/0233104 A1 | 9/2008 | Farmer |
| 2008/0305096 A1 | 12/2008 | Verdegem et al. |
| 2009/0208606 A1 | 8/2009 | Hakansson et al. |
| 2010/0074993 A1 | 3/2010 | Cooreman et al. |
| 2011/0020305 A1 | 1/2011 | Farmer |

FOREIGN PATENT DOCUMENTS

| | | |
|---|---|---|
| JP | 11335285 A | 12/1999 |
| JP | 2000-93162 | 4/2000 |
| JP | 2001252012 A | 9/2001 |
| JP | 2001286278 A | 10/2001 |
| JP | 2001292763 A | 10/2001 |
| JP | 2002522393 | 7/2002 |
| JP | 2004337125 A | 12/2004 |
| JP | 2005137357 A | 6/2005 |
| JP | 2006025621 A | 2/2006 |
| JP | 2006254837 A | 9/2006 |
| JP | 2007000140 A | 1/2007 |
| JP | 2007044014 A | 2/2007 |
| JP | 2007054081 A | 3/2007 |
| JP | 2008013543 A | 1/2008 |
| TW | 1228974 B | 3/2005 |
| WO | WO-8905849 A1 | 6/1989 |
| WO | WO-9314187 A1 | 7/1993 |
| WO | WO-9400019 A1 | 1/1994 |
| WO | WO-9411492 A1 | 5/1994 |
| WO | WO-9611014 A1 | 4/1996 |
| WO | WO-9729762 A1 | 8/1997 |
| WO | WO-9734615 A1 | 9/1997 |
| WO | WO-98/54982 A1 | 12/1998 |
| WO | WO-0007606 A2 | 2/2000 |
| WO | WO-0134168 A1 | 5/2001 |
| WO | WO-2004004747 A1 | 1/2004 |
| WO | WO-2004008870 A1 | 1/2004 |
| WO | WO-2005019417 A2 | 3/2005 |
| WO | WO-2005055934 A2 | 6/2005 |
| WO | WO-2005092122 A1 | 10/2005 |
| WO | WO-2005110445 A2 | 11/2005 |
| WO | WO-2005117926 A1 | 12/2005 |
| WO | WO-2006/090729 A1 | 8/2006 |
| WO | WO-2007012847 A1 | 2/2007 |
| WO | WO-2007/058027 A1 | 5/2007 |
| WO | WO-2008/112296 A1 | 9/2008 |
| WO | WO-2009/029267 A1 | 3/2009 |
| WO | WO-2009/051753 A1 | 4/2009 |

OTHER PUBLICATIONS

*Bergey's Manual of Systematic Bacteriology*, vol. 2, Sneat h et al., eds., Williams & Wilkens, Baltimore, MD, p. 1117 (1986).

Nakamura et al., "Taxonomic Study of *Bacillus coagulans* Hammer 1915 with a Proposal for *Bacillus smithii* sp. nov.", *Inter'l J. Sytematic Bacteriol.*, 38(1):63-73 (1988).

Sawatari, Y. et al., "Development of fermented instant Chinese noodle using Lactobacillus plantarum", *Food Microbiology* 22(6):539-546 (2005).

Allos. "Association Between *Campylobacter* Infection and Guillain-Barre Syndrome." *J. Infect. Dis.* 176(1997):S125-S128.

Amaha et al. Sporulation requirements of *Bacillus coagulans*; var. *thermoacidurans* in complex media. J Bacteriol. Jul. 1956;72(1):34-41.

Baker et al. "Growth Requirements of 94 Strains of Thermophilic Bacilli." *Can. J. Microbiol.* 6(1960):557-563.

Barefoot et al. "Antibiosis Revisited: Bacteriocins Produced by Dairy Starter Cultures." *J. Diary ScL* 76(1993):2366-2379.

Bernet et al. "Adhesion of Human Bifidobacterial Strains to Cultured Human Intestinal Epithelial Cells and Inhibition of Enteropathogen-Cell Interactions." *Appl. Environ. Microbiol.* 59.12(1993): 4121-4128.

Bernet et al. "*Lactobacillus acidophilus* LA 1 Binds to Cultured Human Intestinal Cell Lines and Inhibits Cell Attachment and Cell Invasion by Enterovirulent Bacteria." *Gut.* 35(1994):483-489.

Black et al. "Experimental *Camplylobacterjejuni* Infection in Humans." *J. Infect. Dis.* 157.3(1988):472-479.

Blaser et al. "The Influence of Immunity on Raw Milk-Associated *Campylobacter* Infection." *JAMA.* 257.1(1987):43-46.

Blaser. "*Campylobacter* Species." *Principles and Practice of Infectious Diseases.* Mandell et al.,eds. New York: Churchill Livingstone Inc. 3(1990):1649-1658.

Challa et al. "Bifidobacterium longum and Lactulose Suppress Azoxymethane-Induced Colonic Aberrant Crypt Foci in Rats." *Carcinogenesis.* 18.3(1997):517-521.

Christi et al., "Role of dietary sulphate in the regulation of methanogenesis in the human large intestine", *Gut*, 33:1234-1238 (1992).

Cometta et al. "*Escherichia coli* Resistant to Fluoroquinolones in Patients with Cancer and Neutropenia." *New Engl. J. Med.* 330. 17(1994):1240-1241.

Database WPI Week 198532 Thomson Scientific, London, GB; AN 1985-195034 XP002502608 & *SU* 1 134 151 A (Kiev Food Ind Techn Inst) (Jan. 15, 1985).

De Simone et al. "Effect of *Bifidobacterium bifidum* and *Lactobacillus acidophilus* on Gut Mucosa and Peripheral Blood B Lymphocytes." *Immunopharmacol. ImmunotoxicoL* 14.1&2(1992):331-340.

E. De Veechi and L. Drago "Lactobacillus sporogenes or Bacillus coagulans: Misidentification or Mislabeling" 2006 International Journal of Probiotics and Prebiotics vol. 1 No. 1 pp. 3-10.

Elmer et al. "Biotherapeutic Agents. A Neglected Modality for the Treatment and Prevention of Selected Intestinal and Vaginal Infections." *JAMA.* 275.11(1996):870-876.

English Muffins. *Yakitate/Oishii Tezukurinopan.* (1999):109-111. (Japanese Original and English Translation).

Famularo et al. "Stimulation of Immunity by Probiotics." *Probiotics 2: Applications and Practical Aspects.* Fuller, ed. London: Boundary Row. (1997):133-161.

Fernandez et al. "Effect of Diatomaceous Earth as an Anthelmintic Treatment on Internal Parasites and Feedlot Performance of Beef Steers." *Animal Science* 66.3(1998): 635-641.

Fuller. "Probiotics in Man and Animals." *J. Appl. BacterioL* 66(1989):365-378.

Gandhi. "Lactobacillus Sporogenes: An Advancement in Lactobacillus Therapy." *Townsend Left. Doctors Patients.* 150(1996):108-110.

Gibson et al., Selective stimulation of bifidobacteria in the human colon by oligofructose and inulin, *Gastroenterol.*, 108:975-982 (1995).

Girardin et al. "Antimicrobial Activity of Foodborne *Paenibacillus* and *Bacillus* spp. Against *Clostridium botulinum*." *J. Food Protection.* 65.5(2002):806-813.

Gorbach. "Lactic Acid Bacteria and Human Health." *Ann. Med.* 22(1990):37-41.

Hata et al. "Meningitis Caused by *Bifidobacterium* in an Infant." *Pediatr. Infect. Dis.* 7(1988):669-671.

Hill et al. "Vaginitis: Current Microbiologic and Clinical Concepts." *Can. Med. Assoc. J.* 134(1986):321-331.

(56) References Cited

OTHER PUBLICATIONS

Hyronimus et al. "Coagulin, a Bacteriocin-Like Inhibitory Substance Produced by Bacillus Coagulans 14." *J. Appl. Microbiol.* 85.1(1998):42-50.

Jacobs-Reitsma et al. "The Induction of Quinolone Resistance in *Campylobacter* Bacteria in Broilers by Quinolone Treatment." *Campylobacter, Helicobacters, and Related Organisms*. Newell et al., eds. New YorkL Plenum Press. (1996):307-311.

Ketley. "Pathogenesis of Enteric Infection by *Campylobacter.*" *Microbiol.* 143(1997):5-21.

Kim et al. "Development of Lactobacillus-Sporogenes Resistant to Rifampicin an Antituberculosis Agent." *Korean J. Micro.* 27.2(1989):155-161. (English Abstract Only).

Klaenhammer. "Genetics of Bacteriocins Produced by Lactic Acid Bacteria." *FEMS Microbial. Rev.* 12(1993):39-85.

Koo et al. "Long-Term Effect of Bifidobacteria and Neosugar on Precursor Lesions of Colonic Cancer in CFI Mice." *Nutrit. Rev.* 16(1991):249-257.

Korshunov et al. "Effect of the Combined Administration of Antibiotic Resistant Bifidobacteria and the Corresponding Antibiotics on the Survival of Irradiated Mice." *Zh. MikrobioL Epidemol. ImmunobioL* 5(1982):50-53. (Russian Original and English Abstract).

Lidbeck et al. "Lactobacilli, Anticarcinogenic Activities and Human Intestinal Microflora." *Eur. J. Cancer Prev.* 1(1992):341-353.

Lino et al. "A Study on the Effect of Bacillus Coagulans, a Spore-Forming Lactic Acid Bacteria, in Improving Microflora in the Intestine of a Human." *Prog. Med.* 17(1997):3303-3308. (No English Translation Available).

Lino et al. "A Study on the Effect of Bacillus Coagulans, a Spore-Forming Lactic Acid Bacteria, in Improving the Properties of Feces." *Prog. Med.* 17(1997):3299-3302. (No English Translation Available).

Malin et al. "Promotion of IgA Immune Response in Patients with Crohn's Disease by Oral Bacteriotherapy with Lactobacillus GG." *Ann. Nutr. Metab.* 40(1996)137-145.

Marsh. "Antimicrobial Strategies in the Prevention of Dental Caries." *Caries Res.* 27(1993):72-76.

Mary El-Baz "The Essence of Herbal and Floral Teas" 2006 iUniverse pp. 1 and 2.

Matsumara et al. "Interferon Induction by Murine Peritoneal Macrophage Stimulated with *Lactobacillus gasserL*" *Animal Sci. TechnoL* (Jpn). 63(1992):1157-1159.

Metchinikoff. "Longevity in the Animal Kingdom." *Prolongation of Life*. New York: The Knickerbocker Press. (1910):39-93, 132-183.

Mitchell. "Rearming in the Fight against Bacteria." *Lancet.* 352(1998):462-463.

Murphy et al. "Ciprofloxacin- and Azithromycin-Resistant *Campylobacter* Causing Travelers Diarrhea in U.S. Troops Deployed to Thailand in 1994." *Clin Infect. Dis.* 22(1996):868-869.

Perdigon et al. "Symposium: Probiotic Bacteria for Humans: Clinical Systems for Evaluation of Effectiveness." *J. Dairy Sci.* 78(1995):1597-1606.

Perlman et al. "Persistent *Campylobacterjejuni* Infections in Patients Infected with Human Immunodeficiency Virus (HIV)." *Ann. Intern. Med.* 108(1988):540-546.

Peterson. "Clinical Aspects of *Campylobacterjejuni* Infections in Adults." *Wes. J. Med.* 161.2(1994):148-152.

Peterson. "Rheumatic Manifestations of *Campylobacterjejuni* and *C. fetus* Infections in Adults." *Scand. J. Rheumatol.* 23(1994):167-170.

Piddock. "Quinolone Resistance and *Campylobacter* spp." *J. Antimicrob. Chemother.* 36(1995):891-898.

Rafter. "The Role of Lactic Acid Bacteria in Colon Cancer Prevention." *Scand. J. Gastroenterol.* 30(1995):497-502.

Reddy et al. "Inhibitory Effect of *Bifidobacterium longum* on Colon, Mammary, and Liver Carcinogenesis Induced by 2-Amino-3-methylimidazo[4,5-*f*]quinoline, a Food Mutagen." *Cancer Res.* 53(1993):3914-3918.

Reid et al. "Is There a Role for Lactobacilli in Prevention of Urogenital and Intestinal Infections?" *Clin. Microbiol. Rev.* 3(1990):335-344.

Rogers, R. F. 1978. Bacillus isolates from refrigerated doughs, wheat flour and wheat. Cereal Chem. 55:671-674.

Rowland et al. "Degradation of *N*-Nitrosamines by Intestinal Bacteria." *Appl. Microbiol.* 29(1975):7-12.

Rychen et al. "Effects of Three Microbial Probiotics on Postprandial Porto-Arterial Concentration Differences of Glucose, Galactose and Amino-Nitrogen in the Young Pig." *Brit. J. Nutr.* 74(1995):19-26.

S.D. Singh and G.P. Rao "Stevia: The Herbal Sugar of 21st Century" 2005 Sugar Technology vol. 7 No. 1 pp. 17-24.

Saavedra. "Feeding of *Bifidobacterium bifidum* and *Streptococcus thermophilus* to Infants in Hospital for Prevention of Diarrhoea and Shedding of Rotavirus." *Lancet.* 344(1994):1046-1049.

Salminen et al. "Clinical Uses of Probiotics for Stabilizing the Gut Mucosal Barrier: Successful Strains and Future Challenges." *Antonie Van Leeuwenhoek.* 70(1996):347-358.

Schiffrin et al. "Immune Modulation of Blood Leukocytes in Humans by Lactic Acid Bacteria: Criteria for Strain Selection." *Am. J. Clin. Nutr.* 66(1997):5155-5205.

Sekine et al. "Induction and Activation of Tumoricidal Cells In Vivo and In Vitro by the Bacterial Cell Wall of *Bifdobacterium infantis.*" *Bifidobact. Microflora.* 13.2(1994):65-77.

Shannon. "Multiple-Antibiotic-Resistant *Salmonella.*" *Lancet.* 352(1998):490-491.

Shoenfeld et al. "Guillain-Barre as an Autoimmune Disease." *Int. Arch. Allergy Immunot* 109(1996):318-326.

Smith et al. "Fluoroquinolone-Resistant *Campylobacter* Isolated from Humans and Poultry in Minnesota." *Int. Conf. Emerging Infect. Dis.* 1998:69.

Solis-Pereyra et al. "Induction of Human Cytokines by Bacteria Used in Dairy Foods." *Nutr. Res.* 13(1993):1127-1140.

Sorvillo et al. "Incidence of Campylobacteriosis Among Patients with AIDS in Los Angeles County." *J. Acquired Immune Defic. Syndr.* 4(1991):598-602.

Standiford et al. "Lipoteichoic Acid Induces Secretion of Interleukin-8 From Human Blood Monocytes: A Cellular and Molecular Analysis." *Infect. Immun.* 62.1(1994):119-125.

Sussman et al. "Clinical Manifestations and Therapy of Lactobacillus Endocarditis: Report of a Case and Review of the Literature." *Rev Infect. Dis.* 8.5(1986):771-776.

Suzuki et al. "Purification and Characterization of *Bacillus coagulans* Oligo-1,6-Glucosidase." *Eur. J. Biochem.* 158. 1(1986):77-83.

Tauxe. "Epidemiology of *Campylobacterjejuni* Infections in the United States and Other Industrial Nations." *Campylobacterjejunk* Current Status and Future Trends. Nachamkin et al., eds. Washington, DC:American Society for Microbiology. (1992):9-13.

The Merck Index. Rahway, NJ: Merck & Co., Inc. Windholz et al., eds. 10(1983):549.

Thomason et al. "Bacterial Vaginosis: Current Review With Indications for Asymptomatic Therapy." *Am. J. Obstet Gynecol.* 165(1991):1210-1217.

Tojo et al. "The Effects of *Bifidobacterium breve* Administration on Campylobacter Enteritis." *Acta Paediatr. Jpn.* 29(1987):160-167.

Winberg et al. "Pathogenesis of Urinary Tract Infection-Experimental Studies of Vaginal Resistance to Colonization." *Pediatr. Nephrol.* (1993):509-514.

Yamazaki et al. "Protective Effect of Bifidobacterium-Monoassociation Against Lethal Activity of *Escherichia colL*" *Bifidobacteria Microflora.* 1(1982):55-59.

Zhang et al. "Antimutagenicity and Binding of Lactic Acid Bacteria from a Chinese Cheese to Mutagenic Pyrolyzates." *J. Dairy ScL* 73(1990):2702-2710.

Balasubramaniam et al."High-Pressure Food Processing", Food Sci Tech Int: 14(5):413-418 (2008).

Balasubramaniam et al., "Principles and Application of High Pressure-Based Technologies in the Food Industry", Ann. Rev. Food Sci Technol. 6:435-62.

Daryaei. et al. "Kinetics of Bacillus coagulans spore inactivation in tomato juice by combined pressure-heat treatment" Food Control 30:168-75( 2013).

(56) References Cited

OTHER PUBLICATIONS

El-Baz. "Herbal and Floral Teas, Infusions, or Tisanes?" The Essence of Herbal and Floral Teas. New York: iUniverse.:1-5. (2006).
Rice et al. "Boiling and Bacillus Spores" Emerg Infect Dis. Oct. 2004; 10(10): 18871888 (available at www.ncbi.nlm.nih.gov/pmc/articles/PMC3323245/table/T1/).
Johnson et al." Inactivation of Bacillus coagulans Spores by Pressure-assisted Thermal Processing", Oculus, vol. 1: 35-38 (2010).
Peng et al. "Thermal Inactivation Kinetics of Bacillus coagulans Spores in Tomato Juice", Journal of food protection, vol. 75, No. 7; 1236-1242 (2012).
S.D. Singh and G.P. Rao "Stevia: The Herbal Sugar of 21st Century" ,Sugar Technology vol. 7 No. 1 pp. 17-24 (2005).
Sneath et al., eds. Bergey's Manual of Systematic Bacteriology. Baltimore: Williams and Wilkons. 2:1128(1986).
Wang et al. "Inactivation Kinetics and Reduction of Bacillus Coagulans Spore by the Combination of High Pressure and Moderate Heat", Journal of Food Process Engineering 32 692-708 (2009).
Zimmermann et al."Modeling the inactivation kinetics of Bacillus coagulans spores in tomato pulp from the combined effect of high pressure and moderate temperature", LWT Food Sci and Tech, (53):107-112 (2013).
Hammer, B. W., 1915, Bacteriological Studies on the Coagulation of Evaporated Milk, *Iowa Agric. Expt. Sta. Res. Bull.* 19:119-132.

\* cited by examiner

PROBIOTIC BACILLUS PASTA COMPOSITIONS

RELATED APPLICATIONS

This application claims the benefit of U.S. Ser. No. 61/106,116, filed Oct. 16, 2008, the contents of which are incorporated by reference herein in their entirety.

FIELD OF THE INVENTION

The present application relates to probiotic grain-based compositions comprising lactic acid-producing bacteria.

BACKGROUND OF THE INVENTION

The gastrointestinal microflora plays a number of vital roles in maintaining gastrointestinal tract function and overall physiological health. The growth and metabolism of the many individual bacterial species inhabiting the gastrointestinal tract depend primarily upon the substrates available to them, most of which are derived from the diet. Since probiotics do not generally permanently colonize the host, they need to be ingested regularly for any health promoting properties to persist.

SUMMARY OF THE INVENTION

The invention is based on the discovery that lactic acid-producing bacteria, particularly *Bacillus* species, remain viable and retain their beneficial probiotic properties in food compositions, such as those prepared at high temperatures (e.g., 80, 90, 100, 120, or 150° C.) in boiling water. The invention describes probiotic grain-based compositions. Specifically, the invention provides an isolated *Bacillus coagulans* bacterium in a grain-based composition.

The invention provides compositions comprising a cooked or uncooked composition of a grain and an isolated *Bacillus coagulans* bacterium or spore. The grain is processed, e.g., altered from its naturally-occurring state. For example, the grain is husked, crushed, cracked, or ground. The grain is in the form of flour or a composition made from further manipulation of a grain-based flour. Exemplary grains include wheat, rice, buckwheat, barley, Kamut, corn and oats. Exemplary cooked compositions include pasta, oatmeal, and grits. Suitable pastas include egg pasta, spaghetti (solid, thin cylinders), macaroni (tubes or hollow cylinders), fusilli (spiral-shaped), lasagna (sheets), tagliatelle (flat ribbons), vermicelli (thin spaghetti), ravioli (filled pasta), spätzle and gnocchi. Other suitable pastas include penne rigate (furrowed cylinder-shaped pasta), penne lisce (smooth cylinder-shaped pasta), rotini (corkscrew-shaped pasta), and rigatoni (tube-shaped pasta).

In one aspect, the isolated *Bacillus coagulans* comprise between about 0.01% to about 50% by weight of the grain-based composition. Optionally, the isolated *Bacillus coagulans* comprise between about 0.01% and about 10% by weight of the grain-based composition. Preferably, the isolated *Bacillus coagulans* comprise between about 0.01% and about 0.1% by weight of the grain-based composition.

The invention also provides bacterial species including *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30 or BC$^{30}$, ATCC Designation Number PTA-6086; and GBI-40, ATCC Designation Number PTA-6087; see U.S. Pat. No. 6,849,256 to Farmer).

Optionally, the isolated *Bacillus coagulans* is in the form of a spore. In one aspect, the *Bacillus coagulans* spores activate upon contacting hot liquid. Preferably, the hot liquid is water or milk. Alternatively, the isolated *Bacillus coagulans* is in the form of a vegetative cell. In another aspect, the isolated *Bacillus coagulans* is in the form of a mixture of vegetative cells and spores. Preferably, the *Bacillus coagulans* is predominantly in spore form, e.g., about 75%, about 80%, about 85%, about 90%, about 95%, about 99%, or about 100% spores.

The invention also provides compositions comprising a dry mix for grain-based compositions comprising a grain and an isolated *Bacillus coagulans* bacterium. Also provided are compositions comprising a dry mix for soup comprising a dehydrated matter and an isolated *Bacillus coagulans* bacterium.

Also provided are methods of making a grain-based composition comprising providing a grain-containing base mix and a liquid portion; mixing the grain-containing base mix and the liquid portion to form a batter or dough; combining an isolated *Bacillus coagulans* bacterium with the batter or dough; and heat processing the batter or dough to cook the grain-based composition. Suitable liquid portions include water and milk. In one aspect, the isolated *Bacillus coagulans* is in the form of a spore. In another aspect, the isolated *Bacillus coagulans* is in the form of a vegetative cell. In one aspect, the isolated *Bacillus coagulans* comprise between about 0.1% to about 50% by weight of the grain-based composition. Preferably, the isolated *Bacillus coagulans* comprise between about 1% and about 10% by weight of the grain-based composition. Most preferably, the amount of *Bacillus coagulans* bacteria is about $5 \times 10^7$ colony forming units (CFU) of bacteria per gram of food matrix.

*Bacillus coagulans* bacteria are included in the grain-based or soup compositions of this invention. Bacterial species include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30 or BC$^{30}$, ATCC Designation Number PTA-6086; and GBI-40, ATCC Designation Number PTA-6087; see U.S. Pat. No. 6,849,256 to Farmer).

In one aspect, the isolated *Bacillus coagulans* is in the form of a spore. The invention provides for the activation of *Bacillus coagulans* spores upon heating. Optionally, the isolated *Bacillus coagulans* is in the form of a vegetative cell. In another aspect, the isolated *Bacillus coagulans* is in the form of a mixture of vegetative cells and spores.

The *Bacillus coagulans* Hammer strains of the invention are non-pathogenic and generally regarded as safe for use in human nutrition (i.e., GRAS classification) by the U.S. Federal Drug Administration (FDA) and the U.S. Department of Agriculture (USDA), and by those skilled in the art. Furthermore, the *Bacillus coagulans* Hammer strains of the invention germinate at or below human body temperature, rendering them useful as probiotics. Many *Bacillus coagulans* strains outside the Hammer group have mostly industrial applications, little or no nutritional benefit, and environmental contaminants that have not been evaluated for safety. Moreover, many other non-Hammer strains of *Bacillus coagulans* grow optimally at temperatures that exceed human body temperature and, thus, do not germinate efficiently in the human body. Such strains are less or not suitable as probiotics for human consumption.

Cited publications are incorporated herein by reference. Both the foregoing general description and the following detailed description and examples are exemplary and explanatory only and are not restrictive of the invention as claimed.

DETAILED DESCRIPTION OF THE INVENTION

Figure 1:
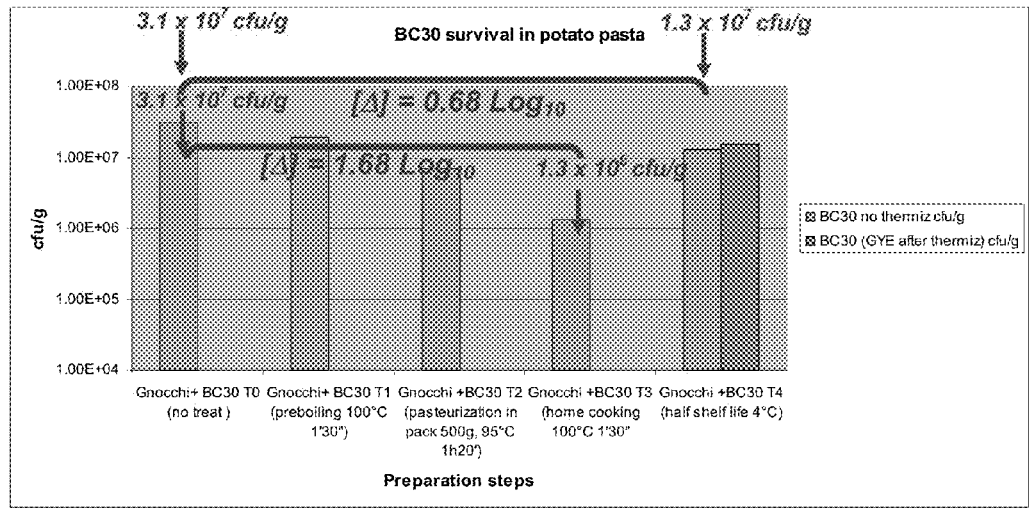
FIG. 1 is a bar graph demonstrating the survival of $BC^{30}$ in gnocchi (potato pasta).

Probiotic organisms are non-pathogenic, non-toxigenic, retain viability during storage, and survive passage through the stomach and small intestine. Non-pathogenic lactic acid-producing bacteria (i.e., "lactic acid bacteria"), such as the exemplary *Bacillus coagulans*, remain viable and retain their beneficial probiotic properties in grain-based and soup compositions, such as those prepared in boiling water. Specifically, the probiotic organisms described herein, e.g., *Bacillus coagulans* strain GBI-30 or $BC^{30}$, ATCC Designation Number PTA-6086, survive the harsh manufacturing and cooking processes of the grain-based and soup compositions described below.

Probiotic Lactic Acid-Producing Bacteria

A probiotic lactic acid-producing bacteria suitable for use in the methods and compositions of the invention produces acid and is non-pathogenic. There are many suitable bacteria identified as described herein, although the invention is not limited to currently known bacterial species insofar as the purposes and objectives of the bacteria is described. The property of acid production is important to the effectiveness of the probiotic lactic acid-producing bacteria of this invention.

The invention provides using a lactic acid-producing bacteria, such as a spore-forming *Bacillus* species, such as *B. coagulans*. Preferably, the spore-forming *Bacillus* species of the invention is *B. coagulans* Hammer.

Exemplary methods and compositions are described herein using *Bacillus coagulans* as a probiotic. Purified and/or isolated *Bacillus coagulans* is particularly useful as a probiotic in grain-based or soup compositions. Probiotic *B. coagulans* is non-pathogenic and is generally regarded as safe (i.e., GRAS classification) by the U.S. Federal Drug Administration (FDA) and the U.S. Department of Agriculture (USDA), and by those skilled in the art.

*Bacillus coagulans* is a non-pathogenic gram positive spore-forming bacteria that produces L(+) lactic acid (dextrorotatory) in fermentation conditions. It has been isolated from natural sources, such as heat-treated soil samples inoculated into nutrient medium (Bergey's Manual off Systemic Bacteriology, Vol. 2, Sneath, P. H. A., et al., eds., Williams & Wilkins, Baltimore, Md., 1986). Purified *B. coagulans* strains have served as a source of enzymes including endonucleases (e.g., U.S. Pat. No. 5,200,336); amylase (U.S. Pat. No. 4,980,180); lactase (U.S. Pat. No. 4,323,651); and cyclo-malto-dextrin glucano-transferase (U.S. Pat. No. 5,102,800). *B. coagulans* has been used to produce lactic acid (U.S. Pat. No. 5,079,164). A strain of *B. coagulans* (referred to as *L. sporogenes*; Sakaguti & Nakayama (ATCC 31284)) has been combined with other lactic acid producing bacteria and *B. natto* to produce a fermented food product from steamed soybeans (U.S. Pat. No. 4,110,477).

Bacterial species include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30, ATCC Designation Number PTA-6086; and GBI-40, ATCC Designation Number PTA-6087; see U.S. Pat. No. 6,849,256 to Farmer).

*Bacillus coagulans* was previously mis-characterized as a *Lactobacillus* and labeled as *Lactobacillus* sporogenes (See Nakamura et al. 1988. *Int. J. Syst. Bacteriol.* 38: 63-73). However, initial classification was incorrect because *Bacillus coagulans* produces spores and excretes L(+)-lactic acid through metabolism. Both of these characteristics provide key features to the utility of *Bacillus coagulans*. These developmental and metabolic aspects required that the bacterium be classified as a lactic acid *Bacillus*. In addition, it is not generally appreciated that classic *Lactobacillus* species are unsuitable for colonization of the gut due to their instability in the harsh (i.e., acidic) pH environment of the bile, particularly human bile. By contrast, *Bacillus coagulans* is able to survive and colonize the gastrointestinal tract in the bile environment and even grown in this low pH range.

Probiotic Activity of *Bacillus coagulans*

It is well-documented clinically that many species of bacterial, mycotic and yeast pathogens possess the ability to cause a variety of gastrointestinal disorders including, but not limited to: disruption of normal gastrointestinal biochemical function, necrosis of gastrointestinal tissues, and disruption of the bioabsorption of nutrients, and like conditions. The probiotic microorganism-containing compositions described herein inhibit these pathogens. Thus, the compositions are useful in the prophylactic or therapeutic treatment of conditions associated with infection by these aforementioned pathogens.

In one aspect, a *Bacillus coagulans* strain is included in the composition in the form of vegetative cells. In another aspect, the *Bacillus coagulans* strain is included in the composition in the form of spores. The invention also provides for including the *Bacillus coagulans* strain in the composition in the form of a powder, a dried cell mass, a stabilized paste, or a stabilized gel.

Because *Bacillus* spores are heat and pressure-resistant and can be stored as a dry powder, they are particularly useful for formulation into and manufacture of products such as the various grain-based and soup compositions described herein. A *Bacillus* species is well suited for the present invention, particularly species having the ability to form spores which are relatively resistant to heat and other conditions, making them ideal for storage (shelf-life) in product formulations, e.g., grain-based and soup compositions. Due to the shelf-stable properties of the *Bacillus coagulans* strains described herein, e.g., *Bacillus coagulans* strain GBI-30 or $BC^{30}$, ATCC Designation Number PTA-6086, the product formulations of the invention are not confined to a refrigerator and may be stored at room temperature.

The *Bacillus coagulans* of the invention survives storage (shelf-life) from about 12 days to about 2 years; from about 1 month to about 18 months; from about 3 months to about 1 year; or from about 6 months to about 9 months.

Anti-Microbial Probiotic Activity

The probiotic organisms described herein, e.g., *Bacillus coagulans* strain GBI-30 or BC$^{30}$, ATCC Designation Number PTA-6086, promote digestive health and support the immune system. The ability of *Bacillus coagulans* to inhibit various bacterial pathogens was quantitatively ascertained by use of an in vitro assay. This assay is part of a standardized bacterial pathogen screen (developed by the U.S. Food and Drug Administration (FDA)) and is commercially available on solid support disks (DIFCO® BACTROL® Antibiotic Disks). To perform the assay, potato-dextrose plates (DIFCO®) were initially prepared using standard procedures. The plates were then individually inoculated with the bacteria (approximately $1.5 \times 10^6$ CFU) to be tested so as to form a confluent bacterial bed.

Inhibition of microorganisms (e.g. gastrointestinal pathogens) by *Bacillus coagulans* was subsequently ascertained by placing approximately $1.8 \times 10^6$ CFU of *Bacillus coagulans* in 10 μl of broth or buffer, directly in the center of the potato-dextrose plate with one test locus being approximately 8 mm in diameter per plate. A minimum of three test loci were used for each assay. The negative control consisted of a 10 μl volume of a sterile saline solution, whereas the positive control consisted of a 1 μl volume of glutaraldehyde. The plates were then incubated for approximately about 18 hr at 30° C., at which time the zones of inhibition were measured. As designated herein, "excellent inhibition" means the zone was 10 mm or greater in diameter; and "good inhibition" means the zone was greater than 2 mm in diameter but less than 10 mm in diameter.

As expected, no "inhibition" was seen with the negative, saline control, and excellent "inhibition" (approximately 16.2 mm diameter; average of three tests) was seen with the positive, glutaraldehyde control. For the enteric microorganisms tested, the following inhibition by *Bacillus coagulans* was found: (i) *Clostridium* species—excellent inhibition; (ii) *Escherichia coli*—excellent inhibition; (iii) *Clostridium* species—excellent inhibition, where the zone of inhibition was consistently greater than 15 mm in diameter. Similarly, excellent inhibition was also seen for the opportunistic pathogens *Pseudomonas aeruginosa*, and *Staphylococcus aureus*. Pathogenic enteric bacteria which were inhibited by *Bacillus coagulans* activity include, but are not limited to: *Staphylococcus aureus*; *Staphylococcus epidermidis*; *Streptococcus pyogenes*; *Pseudomonas aeruginosa*; *Escherichia coli* (enterohemorragic species); numerous *Clostridium* species (e.g., *Clostridium perfingens*, *Clostridium botulinum*, *Clostridium tributrycum*, *Clostridium sporogenes*, and the like); *Gardnereia vaginails*; *Proponbacterium aenes*; *Aeromonas hydrophia*; *Aspergillus* species; *Proteus* species; and *Klebsiella* species.

Micro-Encapsulation

In one aspect, the lactic-acid producing bacteria are incorporated into a microcapsule coating prior to addition to the grain-based composition, using any micro-encapsulation process well-known in the art. The isolated *Bacillus coagulans* are packaged, or encapsulated, within another material in order to protect the bacteria from the surrounding environment. The capsules of the invention range in size from one-thousandth of a millimeter to seven millimeters. The internal ingredients of the microcapsule are released from their shells in various ways, including mechanical rupture of the capsule wall, dissolution of the wall, melting of the wall and diffusion through the wall. Thus, micro-encapsulation provides additional protection to the isolated *Bacillus* bacterium during heat processing of the grain-based compositions of the invention. Physical methods of micro-encapsulation include pan coating, air-suspension coating, centrifugal extrusion, vibrational nozzle, and spray-drying. Chemical methods of micro-encapsulation include interfacial polymerization, in-situ polymerization, and matrix polymerization.

Alternatively, the lactic-acid producing bacteria is added to the grain-based composition without micro-encapsulation.

Probiotic Grain-Based and Soup Compositions

The invention is directed to the surprising discovery that lactic acid-producing bacteria, particularly *Bacillus* species, remain viable and retain their beneficial probiotic properties in grain-based and soup compositions, such as those prepared in boiling water. The compositions are prepared by combining dry matter and a liquid, e.g., water or milk. In one aspect, the composition is prepared by combining dry matter and a liquid, and heating the resulting combination. Optionally, the combination is heated (heat-processed) using applied heat, a flame, or a microwave. The grain-based or soup composition is boiled in hot water, e.g., stovetop boiling, addition of boiling water to a container, or microwaving the grain-based or soup composition along with water. Preferably, boiling water (about 100° C.) is added to a combination of grain-based composition and *Bacillus coagulans* bacteria.

In one aspect, at least about 5%-25% of the bacteria are viable after heating, e.g., at least about 25%-50%; at least about 50% to 75%; or at least about 75%-99% of the bacteria are viable after heating. As the recommended dietary allowances (RDA or recommended daily intake; RDI) is about $1 \times 10^9$ bacterium (according to EU guidelines), preferably, the grain-based or soup composition comprises at least about $1 \times 10^9$ viable bacteria after heating. In another aspect, the grain-based or soup composition comprises at least about $1 \times 10^6$ to $1 \times 10^7$; at least about $1 \times 10^7$ to $1 \times 10^8$; or at least about $1 \times 10^8$ to $1 \times 10^9$ viable bacteria after heating.

The compositions are formulated in many configurations, because the bacterium is present as a vegetative cell or as a spore, or both, depending on the species and form of the probiotic organism. The cells/spores are formulated in a variety of compositions suited for use in a grain-based or soup composition. In one aspect, the bacterium is present as a mixture of spores and vegetative cells. In another aspect, the bacterium is present as at least 90% spores, e.g., 95%, 98%, or 99% spores. Optionally, prior to addition to the grain-based or soup compositions of the invention, the *Bacillus coagulans* cells are cultured in liquid in the absence of or with limited quantities of a food source to induce sporulation. In another aspect, heat gun spray drying kills about 50%, about 75%, about 90%, about 95%, or about 99% of vegetative cells prior to addition to the grain-based or soup compositions of the invention.

Grain-based compositions, such as those described herein, are made from a variety of grains known to those skilled in the art. Suitable grains include rice, wheat, maize, barley, rye, oats, buckwheat, sorghum, millets, triticale, fonio, and quinoa. Other types of grains used to make the grain-based compositions of the invention include teff, wild rice, and durum.

Exemplary grain-based compositions include pasta, oatmeal, grits, cereal, etc. The invention provides probiotic-enhanced pasta, e.g., isolated *Bacillus coagulans* and pasta. Pasta (Italian for "dough") is a generic term for Italian variants of noodles, food made from a dough of flour, water and/or eggs. Pasta is cooked in hot water/boiling water prior to consumption. The probiotic organisms described herein, e.g., *Bacillus coagulans* strain GBI-30 or BC$^{30}$, ATCC Designation Number PTA-6086, uniquely survive the harsh manufacturing and cooking processes of the grain-based and soup compositions. In one aspect, the pasta is the primary ingredient, served with sauce or seasonings. Common varieties of pasta include tubular pasta, straight round rod pasta, ribbon pasta, micro pasta, stuffed pasta, and irregular-shaped pasta. Exemplary pastas include spaghetti (solid, thin cylinders), macaroni (tubes or hollow cylinders), fusilli (spiral-shaped), lasagna (sheets), tagliatelle (flat ribbons), vermicelli (thin spaghetti), and ravioli (filled pasta). Other suitable pastas include penne (cylinder-shaped pasta), rotini (corkscrew-shaped pasta), and rigatoni (tube-shaped pasta). In Italy, penne are produced in two variants: "penne lisce" (smooth) and "penne rigate" (furrowed), the latter having ridges on each noodle. Two other noodles, gnocchi and spätzle, are sometimes counted as pasta because they are traditional in Italy; however, their "native" distributions (and perhaps their origins) are outside Italy, and these noodles have more in common with dumplings than with typical pasta. The two basic styles of pasta are dried and fresh. Dried pasta has a firmer, denser texture when cooked and is suited to chunky, meaty or oily sauces. Fresh pasta has a softer, more absorbent texture and is suited to buttery or creamy sauces or sauces with delicate flavors. There are also variations in the ingredients used in pasta. The time for which pasta can be stored varies from days to years depending upon whether the pasta is made with egg or not, and whether it is dried or fresh.

Many ingredients are used to make pasta dough, ranging from a simple flour and water mixture, to those that call for the addition of eggs, spices and cheeses, or even squid ink to the dough. Optionally, the pasta contains a filling, e.g., cheese, vegetables, fruit, and/or meat. In one aspect, dry pasta is made from durum wheat or semolina flour. Durum flour has a yellow tinge in color. Alternatively, dry pasta is made from other types of flour (such as farina), which yields a softer product. Particular varieties of pasta may also use other grains and/or milling methods to make the flour. Some pasta varieties, such as Pizzoccheri, are made from buckwheat flour. Various types of fresh pasta include eggs (egg pasta). Gnocchi are often considered pasta dishes, although they are quite different in ingredients (mainly milled potatoes).

Also provided are probiotic grain-based compositions in the form of oatmeal with isolated *Bacillus coagulans*. Oatmeal is a product of ground oat groats (i.e., oat-meal, cornmeal, peasemeal, etc.) or a porridge made from this product (also called oatmeal cereal). In regions such as the United States and Canada, "oatmeal" can refer to other products made from oat groats, such as cut oats, crushed oats, and rolled oats. The groats are coarsely ground to make oatmeal, or cut into small pieces to make steel-cut oats, or steamed and rolled to make rolled oats. In the case of rolled oats (old-fashioned oats), oat groats are steamed, pressed with a roller, and dried. Rolled oats take about 15 minutes to cook. The quick-cooking rolled oats ("quick oats") are cut into small pieces before being steamed and rolled. "Instant" oatmeal is pre-cooked and dried. Optionally, the oatmeal includes: sweetener and flavor additives. Suitable sweeteners and flavor additives include salt, white sugar, brown sugar, stevia, cinnamon, honey, jam, molasses, maple syrup, butter, chocolate, soy sauce, soy milk, milk, vinegar, condensed or evaporated milk, and cream. Various types of fruit and nuts are also often added, including: strawberries, blueberries, apples, peaches, mangos, bananas, raisins, dried cherries, dried cranberries, pecans, walnuts, and peanut butter. Oatmeal is used to make porridge, as an ingredient as in oatmeal cookies and oat cakes, or as an accent as in the topping on many oat bran breads and the coating on Caboc cheese. Oatmeal is used as a thickener in some foods such as canned chili con came. Oatmeal is also used in some alcoholic drinks, cosmetics, soaps, external medical treatments, and is sometimes added to animal feed products.

In another aspect, the probiotic composition of the invention is grits with isolated *Bacillus coagulans*. Grits is an American Indian corn-based food common in the southern United States, consisting of coarsely ground corn. Traditionally the corn for grits is ground by a stone mill. The results are passed through screens, with the finer part being corn meal, and the coarser part being grits.

Also provided are probiotic instant soups including isolated *Bacillus coagulans* in soups that require hot water. Soup is a food that is made by combining ingredients such as meat and vegetables in stock or hot/boiling water, until the flavor is extracted, forming a broth. Traditionally, soups are classified into two broad groups: clear soups and thick soups. Thick soups are classified depending upon the type of thickening agent used: purées are vegetable soups thickened with starch; bisques are made from puréed shellfish thickened with cream; cream soups are thickened with béchamel sauce; and veloutés are thickened with eggs, butter and cream. Other ingredients commonly used to thicken soups and broths include rice, flour, and grain. Oriental-style soup mixes containing ramen noodles are marketed as an inexpensive instant lunch, requiring only hot water for preparation. Various types of soups include tomato soup, cream of mushroom soup, chicken noodle soup, vegetable beef soup, minestrone soup, leek and potato soup, lentil soup, fish soup, miso soup, pea soup, fruit soup, clam chowder, gumbo, and bisque. Many soups, such as vegetable, chicken base, potato, pasta and cheese soups, are also available in dry mix form, ready to be served by adding hot water. Dry mix soup includes dehydrated matter, e.g., dehydrated meat, such as poultry and beef, dehydrated vegetables, dehydrated herbs, dehydrated spices, dehydrated noodles, etc. A packet of dry soup stock (e.g., ramen) typically does not contain water. The instant soup is prepared by adding water first, and then heating the product for a short time (usually 3-5 minutes) or by adding hot water directly to the dry soup mix. Instant soup can also be preserved into a dry powder which can be stored in, e.g., a packet or a cup. *Bacillus coagulans* bacteria in the form of spray-dried powder is added prior to or subsequent to addition of the dry mix soup powder to hot water.

In one aspect, *Bacillus coagulans* bacteria in the form of a spray-dried powder is included in or on the surface of the probiotic grain-based composition described herein. Preferably, the isolated *Bacillus coagulans* is in the form of a spore. The isolated *Bacillus coagulans* are at least 85%, at least 90%, at least 95%, or at least 99% pure spores. Alternatively, the isolated *Bacillus coagulans* is in the form of a vegetative cell. In one aspect, the isolated *Bacillus coagulans* are at least 85%, at least 90%, or at least 95% pure vegetative cells. In another aspect, the isolated *Bacillus coagulans* is in the form of a mixture of vegetative cells and spores. The *Bacillus coagulans* mixture is 90% spores, 10% vegetative cells; 75% spores, 25% vegetative cells; 60% spores, 40% vegetative cells; 50% spores, 50% vegetative cells; 60% vegetative cells, 40% spores; 75% vegetative cells; 25% spores; or 90% vegetative cells, 10% spores.

The *Bacillus* and/or *Bacillus coagulans* isolated active agent is applied using any of a variety of known methods including, for example, applying a powder, spray-drying the probiotic onto the grain-based or dry mix soup composition, or soaking the composition in a solution containing the probiotic. Optionally, the *Bacillus* bacterium is added to the dough and dried into the product (e.g., pasta). Alternatively, the *Bacillus* bacterium is mixed with the dry mix product (e.g., oatmeal or soup) prior to boiling in water. In another aspect, *Bacillus coagulans* bacteria in the form of spray-dried powder is added directly to the grain-based or soup composition itself. In yet another aspect, maltodextrin along with *Bacillus coagulans* bacteria in the form of spray-dried powder is added directly to the grain-based or soup composition itself. Optionally, about $5 \times 10^7$ CFU *Bacillus coagulans* bacteria (per gram of food matrix) in the form of spray-dried powder along with maltodextrin is added directly to the food composition itself.

Any of a variety of methods for placing the bacterial composition into a grain-based or soup composition can be used. However, preferred methods include a "spray-dry" method in which the compositions are exposed in a low humidity chamber to an atomized mix containing a liquid composition, where the chamber is subsequently exposed to approximately 80-110° F. to dry the liquid, thereby impregnating the material of grain-based or dry mix soup composition with the components.

A typical concentration is from approximately $1 \times 10^7$ to $1 \times 10^{12}$ CFU; $1 \times 10^8$ to $1 \times 10^{11}$ CFU; or $1 \times 10^9$ to $1 \times 10^{10}$ CFU of viable bacterium or spores/g of food matrix. Following drying, the food is ready for immediate use or for storage in a sterile package, e.g., a 3-ounce package, a 6-ounce package, a 9-ounce package, a 12-ounce package, a 15-ounce package, an 18-ounce package, or a 24-ounce package.

The active ingredients (i.e., live bacteria or extracellular components), comprise between about 0.01% to about 10%; 0.01% to about 1%; or about 0.05% to about 0.1% by weight of the probiotic grain-based or soup composition. Optionally, the isolated *Bacillus coagulans* comprise about 1 mg to about 10 g; about 10 mg to about 1 g; or about 25 mg to about 75 mg by weight of the probiotic composition. Most preferably, the amount of *Bacillus coagulans* bacteria is about $5 \times 10^7$ colony forming units (CFU) of bacteria per gram of food matrix.

In one aspect, the amount of bacteria is about $10^4$ to $10^{14}$ colony forming units (CFU) of bacteria per gram of probiotic composition (i.e., vegetative cells and/or bacterial spores), preferably $10^5$ to $10^{13}$ CFU/g of food matrix. Alternatively, the concentrations are $10^8$ to $10^{13}$ CFU/g; $10^9$ to $10^{12}$ CFU/g; or $10^{10}$ to $10^{11}$ CFU/g of food matrix. In one aspect, the amount of bacteria is about $1 \times 10^6$ CFU per gram of food matrix. The actual amount in a grain-based or soup composition will vary depending upon the amounts of composition to be dispersed into the food composition and upon routes of dispersal.

In one aspect, the invention provides for storing the grain-based or dry mix soup composition in a sterile package at room temperature prior to consumption. Alternatively, the composition is consumed immediately.

In another aspect, the composition comprises at least 85%, at least 90%, at least 95% or 100% isolated *Bacillus coagulans* spores.

By way of example, and not of limitation, *Bacillus coagulans* spores may be incorporated into any type of dry or lyophilized product which is dissolved or mixed with hot water, so long as the temperature of the *Bacillus coagulans* spore-containing mixture is raised to the required heat-shock temperature (i.e., 80° C. for 5 minutes) necessary for germination of the spores. The *Bacillus coagulans* spores may either be incorporated into the dry or lyophilized product by the manufacturer of the product or by the consumer during preparation. These dry or lyophilized products include, but are not limited to: dry mix soups, pasta, oatmeal, grits, etc. The grain-based or soup composition is subsequently boiled in hot water, e.g., stovetop boiling, addition of boiling water to a container, or microwaving the grain-based or soup composition along with water.

In one aspect, the *Bacillus coagulans* spores survive storage (shelf-life), i.e., retain viability or the ability to germinate at physiological conditions (e.g., ingestion), from about 12 days to about 2 years; from about 1 month to about 18 months; from about 3 months to about 1 year; or from about 6 months to about 9 months.

Example 1

Preparation of *Bacillus coagulans* Cultures

*Bacillus coagulans* Hammer bacteria (ATCC Accession No. 31284) was inoculated and grown to a cell density of about $10^8$ to $10^9$ cells/ml in nutrient broth containing 5 g Peptone, 3 g Meat extract, 10-30 mg $MnSO_4$, and 1,000 ml distilled water, adjusted to pH 7.0, using a standard airlift fermentation vessel at 30° C. The range of $MnSO_4$ acceptable for sporulation is 1 mg/l to 1 g/l. The vegetative cells can actively reproduce up to 45° C., and the spores are stable up to 90° C. After fermentation, the *B. coagulans* bacterial cells or spores are collected using standard methods (e.g., filtration, centrifugation) and the collected cells and spores can be lyophilized, spray-dried, air-dried or frozen. As described herein, the supernatant from the cell culture is collected and used as an extracellular agent secreted by *B. coagulans*.

A typical yield from the above culture is in the range of about $10^9$ to $10^{10}$ viable spores and more typically about 100 to 150 billion cells/spores per gram before drying. Spores maintain at least 90% viability after drying when stored at room temperature for up to ten years, and thus the effective shelf life of a composition containing *B. coagulans* Hammer spores at room temperature is about 10 years.

Example 2

Preparation of *Bacillus coagulans* Spores

A culture of dried *B. coagulans* spores was prepared as follows. Ten million spores were inoculated into a one liter culture containing 24 g potato dextrose broth, 10 g of enzymic-digest of poultry and fish tissue, 5 g of FOS and 10 g $MnSO_4$. The culture was maintained for 72 hours under a high oxygen environment at 37° C. to produce culture having about 150 billion cells per gram of culture. Thereafter, the culture was filtered to remove culture medium liquid, and the bacterial pellet was resuspended in water and freeze-dried. The freeze-dried powder is then ground to a fine powder using standard good manufacturing practice (GMP).

Example 3

Bacillus coagulans Spores Survive in the Gastric Environment

This study was performed in order to determine the survivability rate of *Bacillus coagulans* spores as they pass through the stomach. Samples of *Bacillus coagulans* spores were subjected to a simulated gastric environment for varying lengths of time in order to attain their survivability rate. First, a homogeneous sample of raw material *Bacillus coagulans* of at least 12 grams was prepared. Saline solution at pH 1 was prepared using 3N HCl (150 mls each into six 250 ml media bottles) and sterilized. Additional saline solutions with pH 2 and 3 were prepared similarly, resulting in 6 sterile 250 ml bottles, each containing 150 ml pH adjusted saline. Six sterile 250 ml media bottles each containing 150 ml normal saline solution were prepared and sterilized. Phosphate buffer (~400 ml) was prepared at pH 7.2. Test tubes (24) were prepared and sterilized, each containing 9 ml of phosphate buffer pH 7.2. Test tubes (120) were prepared, each containing 9 ml of normal saline. GYE (glucose-yeast extract) agar medium was prepared and sterilized and cooled to 45° C. in a water bath. Samples (24) of raw material were weighed, each ~500 milligrams (theoretically equivalent to 10 billion spores). The samples were added to media bottles at 37° C. and incubated half for 20 minutes the other half for 120 minutes. After 20 and 120 minutes incubation, respectively, the samples were mixed to uniformity and pipet 1 ml into 9 ml of sterile phosphate buffer pH 7.2. After all 12 samples from each time point were placed into test tubes containing sterile phosphate buffer, serial dilutions were made until 6 tubes had been used for each sample. The final dilution for the final two test tubes were $3 \times 10^7$ and $3 \times 10^8$, which gave a count of roughly 300 and 30 CFU, respectively. The final 2 test tubes from each sample were placed into 70° C. water bath for 30 minutes. After 30 minutes, they were cooled immediately to 45° C. Three sterile petri plates per tube were set out. 1.0 ml from the heat-treated tube was added into each petri plate, then 15 ml of sterile molten GYE Agar medium (at 45° C.) was poured into each of the petri plates and mixed thoroughly. When solidified, the plates were incubated in an inverted position for 48 hours at 40° C. The individual colonies were counted. Results were expressed as CFU per gram as shown in Table 1 below. $1.0E+10=1 \times 10^{10}$.

TABLE 1

| Sample | 20 Minutes Incubation Spore Count, CFU/gram | 120 Minutes Incubation Spore Count, CFU/gram |
|---|---|---|
| Normal Saline - A | 1.90E+10 | 1.88E+10 |
| Normal Saline - B | 2.12E+10 | 2.00E+10 |
| Normal Saline - C | 1.64E+10 | 2.06E+10 |
| Average | 1.89E+10 | 1.98E+10 |
| Saline pH 1.0 - D | 2.08E+09 | 5.98E+07 |
| Saline pH 1.0 - E | 1.47E+09 | 0.00E+00 |
| Saline pH 1.0 - F | 3.59E+09 | 0.00E+00 |
| Average | 2.38E+09 | 1.99E+07 |
| Saline pH 2.0 - G | 3.63E+09 | 3.46E+09 |
| Saline pH 2.0 - H | 4.47E+09 | 2.48E+09 |
| Saline pH 2.0 - I | 3.58E+09 | 2.82E+09 |
| Average | 3.89E+09 | 2.92E+09 |
| Saline pH 3.0 - J | 1.65E+10 | 1.13E+10 |
| Saline pH 3.0 - K | 1.35E+10 | 1.11E+10 |
| Saline pH 3.0 - L | 1.80E+10 | 1.39E+10 |
| Average | 1.60E+10 | 1.21E+10 |

Example 4

Bacillus coagulans Retain Viability in Gnocchi (Potato Pasta)

The purpose of the following study was to determine the survivability rate of GBI-30 (*Bacillus coagulans*-30; $BC^{30}$) in gnocchi (potato pasta) after cooking and pasteurization. $BC^{30}$ was mixed into gnocchi (potato pasta) at the dose of $5 \times 10^7$ CFU/g of food matrix, spray dried, and boiled in water at 100° C. for 1 minute and 30 seconds. The potato pasta was subsequently pasteurized for 1 hour and 20 minutes at 95° C. Following pasteurization, the potato pasta was cooked at 100° C. for 1 minute and 30 seconds to simulate home cooking. The pasta was stored at 4° C. for 30 days (shelf life is 60 days), heat shocked at approximately 80° C. for about 5 minutes, and placed in GYE agar medium. The results demonstrate that approximately $1.3 \times 10^7$ CFU of *Bacillus coagulans* per gram of food matrix survived even after storage for about 30 days. Comparable results were observed after heat shock (thermiz), suggesting that after the cooking process, the pasta comprises mostly *Bacillus coagulans* spores and few vegetative cells. The potato pasta was packaged in a modified atmosphere. The water activity ($A_w$) of the composition was approximately 0.95%. The data in FIG. 1 show that after pre-boiling, pasteurization, and cooking, the amount of $BC^{30}$ in the potato pasta was $3 \times 10^6$ CFU/g of food matrix, suggesting that the approximate daily dose of probiotics in 100 g of gnocchi is about $1.3 \times 10^9$ CFU or 100% RDA (1 billion viable cells is the recommended dose in EU guidelines).

Example 5

Bacillus coagulans Retain Viability in Fresh Egg Pasta

Figure 2:
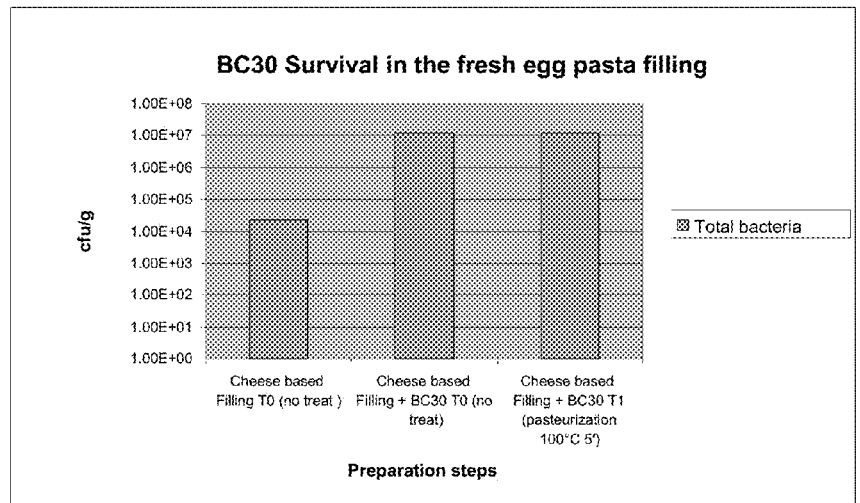
FIG. 2 is a bar chart illustrating the survival of $BC^{30}$ in fresh egg pasta filling. Left bar: untreated pasta with cheese-based filling (containing bacterial cheese cultures); middle bar: pasta with cheese-based filling treated with $BC^{30}$; right bar: pasta with cheese-based filling treated with $BC^{30}$ and pasteurized at 100° C. for 5 minutes.

This study was performed in order to determine the survivability rate of GBI-30 (*Bacillus coagulans*-30; $BC^{30}$) in fresh egg pasta after pasteurization. $BC^{30}$ was mixed into the fresh egg pasta with cheese, vegetables, and meat filling at the dose of $5 \times 10^7$ CFU/g of food matrix. The fresh egg pasta was subsequently spray dried and pasteurized for approximately 5 minutes at 100° C. The shelf life of the fresh egg pasta was 50 days. The pasta was packaged in a modified atmosphere. The water activity ($A_w$) of the composition was approximately 0.92-0.97%. The results illustrated in FIG. 2 demonstrate that approximately $2 \times 10^7$ CFU of $BC^{30}$ survived the pasteurization described above, indicating that *Bacillus coagulans* retain viability in the fresh egg pasta.

Example 6

Survival of Heat-Activated Bacillus coagulans

The ability of GBI-30 (*Bacillus coagulans*-30; $BC^{30}$) in oatmeal to survive heating via microwave was determined. Table 2 demonstrates that approximately 82% of the $BC^{30}$ alone survived microwaving for 1 minute and 50 seconds. As shown in Table 2, approximately 79% of the initial *Bacillus coagulans* bacteria in oatmeal survived after microwaving for 1 minute and 50 seconds, suggesting that *Bacillus coagulans* retain viability in oatmeal after cooking Table 2 shows the survival of BC30 after heat treatment under various conditions.

TABLE 2

| Sample Description | Testing Method | CFU/Spec | Sample Size | Total Count | % of Spec |
|---|---|---|---|---|---|
| A: BC30, heat activation | Total Plate Count | 11900000000 | 1 g | 11900000000 | 100% |
| B: BC30, microwave | Total Plate Count | 11900000000 | 1 g | 9750000000 | 82% |
| C: BC30 + oatmeal, microwave | Total Plate Count | 11900000000 | 1 g | 9350000000 | 79% |

A: BC30 1 g + 10 ml water, 75 C. 30 min, cooled to 45 C., serial dilution, total plate count.
B: BC30 1 g + 250 ml water, microwave 1 min 50 second, serial dilution, total plate count.
C: BC30 1 g + 1 serving of oatmeal (35.6 g) + 250 ml water, microwave 1 min 50 second, serial dilution, total plate count.

Example 7

Bacillus coagulans in Dry Turtle Island Soup Mix

The probiotic Bacillus coagulans of the invention was added to dry Turtle Island soup mix in the amount indicated in Table 3. Table 3 is a chart indicating the number of colony forming units (CFU) of $BC^{30}$ per serving of dry soup mix.

TABLE 3

| | Sample Description | Weight/ serving | Amount of BC 30 | CFU/ serving |
|---|---|---|---|---|
| 1 | Dry Soup Mix | 38.2 gram | 0.02 gram | $2.81 \times 10^8$ |
| 2 | Dry Soup Mix | 38.3 gram | 0.02 gram | $2.26 \times 10^8$ |
| 3 | Dry Soup Mix | 39.1 gram | 0.5 gram | $7.05 \times 10^9$ |

Example 8

Bacillus coagulans Retain Viability in Durum Wheat Semolina Pasta

The purpose of the following study was to determine the survivability rate of GBI-30 (Bacillus coagulans-30; $BC^{30}$) in durum wheat semolina pasta after cooking $BC^{30}$ was mixed into the durum wheat semolina pasta at the dose of about $4 \times 10^8$ CFU/serving (about $7 \times 10^6$ CFU/g of food matrix (about 30 mg of $BC^{30}$); serving size is about 56 grams). The composition was extruded at 37-38° C., followed by 20 hours of drying at 50° C. Table 4 shows the survival of $BC^{30}$ after manufacturing the dry pasta and after cooking the dry pasta via boiling for about 8 minutes. The results shown in Table 4 demonstrate that approximately 55% of $BC^{30}$ survive the manufacturing process, while approximately 30% of $BC^{30}$ survive the cooking process, indicating that Bacillus coagulans $BC^{30}$ retain viability in durum wheat semolina pasta.

TABLE 4

| Sample Description | CFU/ Spec | Sample Size | Total Count | % of Spec |
|---|---|---|---|---|
| Dry pasta (uncooked) | $4 \times 10^8$ | 56 g | $2.2 \times 10^8$ | 55% |
| Dry pasta (cooked) | $4 \times 10^8$ | 56 g | $1.2 \times 10^8$ | 30% |

What is claimed is:

1. A food composition comprising a processed grain and isolated Bacillus coagulans spores, wherein said composition comprises pasta, and wherein said isolated Bacillus coagulans is GBI-30 strain (ATCC Designation Number PTA-6086).

2. The composition of claim 1, wherein said pasta is selected from the group consisting of spaghetti, lasagna, egg pasta, spätzle, penne rigate, rotini, rigatoni, and gnocchi.

3. The composition of claim 1, wherein said isolated Bacillus coagulans spores comprise between 0.01% and 10% by weight of said composition.

4. The composition of claim 1, wherein said Bacillus coagulans spores activate upon contacting hot liquid.

5. The composition of claim 4, wherein said hot liquid is water or milk.

6. A food composition comprising a dry mix for a grain-based composition comprising a grain and isolated Bacillus coagulans spores, wherein said grain-based composition comprises pasta, and wherein said isolated Bacillus coagulans is GBI-30 strain (ATCC Designation Number PTA-6086).

7. The composition of claim 1, wherein said composition comprises dried pasta.

8. The composition of claim 1, wherein said composition comprises pasta dough.

9. The composition of claim 1, wherein said composition comprises cooked pasta.

10. The composition of claim 1, wherein said composition has been subject to a temperature selected from the group consisting of 100° C., 120° C., and 150° C.

11. The composition of claim 1, wherein said composition is subject to a temperature selected from the group consisting of 100° C., 120° C., and 150° C.

12. The composition of claim 1, wherein at least about 5% to 25% of said Bacillus coagulans spores remain viable after being subject to a temperature of 100° C. for one minute in water.

13. The composition of claim 6, wherein at least about 5% to 25% of said Bacillus coagulans spores remain viable after being subject to a temperature of 100° C. for one minute in water.

14. The composition of claim 1, wherein at least about 5% to 25% of said Bacillus coagulans spores remain viable after being subject to a temperature of 100° C. for eight minutes in water.

15. The composition of claim 6, wherein at least about 5% to 25% of said Bacillus coagulans spores remain viable after being subject to a temperature of 100° C. for eight minutes in water.

* * * * *